United States Patent [19]

Hixson, Sr.

[11] Patent Number: 5,189,686
[45] Date of Patent: Feb. 23, 1993

[54] ADJUSTABLE MOUNTING BASE FOR MAMMOGRAPHIC SPOT COMPRESSION AND MAGNIFICATION PLATFORM

[75] Inventor: Gordon L. Hixson, Sr., Chattanooga, Tenn.

[73] Assignee: American Mammographics, Inc., Chattanooga, Tenn.

[21] Appl. No.: 797,386

[22] Filed: Nov. 25, 1991

Related U.S. Application Data

[63] Continuation-in-part of Ser. No. 736,068, Jul. 25, 1991, Pat. No. 5,136,623.

[51] Int. Cl.⁵ .............................................. G21K 1/02
[52] U.S. Cl. ..................................... 378/37; 378/167; 378/172
[58] Field of Search ................. 378/37, 167, 170, 172, 378/177, 178, 187, 186

[56] References Cited

U.S. PATENT DOCUMENTS 4,947,417 8/1990 Hartwell ............................... 378/37

*Primary Examiner*—David P. Porta
*Assistant Examiner*—Don Wong
*Attorney, Agent, or Firm*—Alan Ruderman

[57] ABSTRACT

A spot compression and magnification device for use with mammographic units to aid in the spot compression of a female patient's breast to obtain a high degree of focal breast compression and a high quality x-ray image of a suspicious mass within the breast. The device has a base including an open bottom and an upstanding pedestal opening into the base, the pedestal having a flat top surface so that an air gap is provided between the top surface of the pedestal and the surface of the imaging platform or cassette cover of a conventional mammographic unit. The pedestal has a sustantially truncated conical form while the base has a substantially truncated pyramid configuration. Clamping handles are resiliently attached to portions of the base to permit the handles to be pulled away from the base and be urged into clampimg engagement with a small size cassette cover using a first set of tongues on the handles acting in conjunction with the bottom edge of the base or into clamping engagement with a larger size cassette cover using a second set of tongues on the handle acting in conjunction with a bottom surface of the first tongues.

5 Claims, 2 Drawing Sheets

ADJUSTABLE MOUNTING BASE FOR MAMMOGRAPHIC SPOT COMPRESSION AND MAGNIFICATION PLATFORM

REFERENCE TO RELATED APPLICATIONS

This application is a continuation-in-part of copending U.S. application Ser. No. 07/736,068 filed Jul. 25, 1991 now U.S. Pat. No. 5,136,623.

BACKGROUND OF THE INVENTION

This invention relates to a spot compression and magnification platform for aiding in compressing a small area of the breast of a woman undergoing a mammographic examination to displace glandular structure and enhance the quality of the image made by the mammography x-ray apparatus, and more particularly to a mounting base for adjustable attachment of the spot compression and magnification platform to the supporting platform of the mammographic unit.

The x-ray detection of the breast, known as mammography, can provide a sensitive and satisfactory means for examining women when screening for breast cancer, an abnormality which affects a significant percentage of the female population. The predictability of the results of the procedure, which is predicated upon an interpretation of the x-ray image produced, and thus the quality of the image, may in certain cases be indefinite and thus inconclusive. For example, many of the abnormal or suspicious soft tissue densities demonstrated are neither clearly benign nor malignant. Cancers, benign tumors, cysts, and asymmetrical areas of glandular tissue can all have similar appearances. Consequently, breast biopsies subsequent to mammographic examination using conventional compression of the breast disclose a relatively low positive yield for cancer, ranging from ten percent to thirty percent. Thus, it has been demonstrated that equivocal mammographic abnormalities require supplemental diagnostic procedures to avoid unnecessary breast biopsy.

One of the most useful additional procedures is a spot compression view which is performed with a small compression paddle to compress only a small area of the breast to increase the accuracy of the image and confidence of the interpretation, the small compression paddle being substituted for a larger conventional paddle. A spot compression view spreads apart glandular structures which can simulate a mass or hide the margins of a true mass. Such views can better define a mass seen on a routine view, and also distinguish abnormalities from those caused by superimposition of normal breast tissue. In the majority of cases a spot compression view shows the suspicious soft tissue density to be benign thereby eliminating unnecessary additional mammographic examination necessitating an additional dose of x-rays, and/or breast biopsy.

Conventional mammographic views utilize a large flat compression paddle which is pushed against the upper portion of the breast to compress the breast between the paddle and the imaging platform of the mammography apparatus. A smaller compression paddle is conventionally used to compress a small area over a potential abnormality in the breast when spot compression views are performed. All of the known compression paddles in the prior art are mechanically attached for use to the adjustable vertical column of the mammographic unit above the breast. When a suspicious area is located on an x-ray, the standard paddle is removed and replaced by the smaller spot compression paddle, which as aforesaid provides a localized compression and a higher quality view by moving normal glandular structure or tissue from dispositions which may be superimposed relative to the area of the breast which requires closer examination.

Many of the older mammographic units in operation do not have the capability of readily accepting spot compression paddles which, it is believed, are available only for the newer mammographic units. Because of the enormous capital expense required for acquiring such units, many hospitals and other diagnostic facilities having the older mammographic units have not made, and may be unable to make, such expenditures as are necessary. Additionally, even with those newer units that have spot compression paddles, because of the normal shape of a breast, i.e., the upper portion of the breast has a greater slope than the lower portion which is substantially horizontal, compression of the breast at the upper portion against the imaging platform may not provide as much clarity to the image as would appear to be the case were the breast to undergo additional spot compression from the lower portion. At least one manufacturer provides a rigid stool-like member for increasing the magnification of the image, but not for spot compression of the breast, the member being attachable to the image platform and having a large top portion on which the breast rests while the image is being made.

In U.S. Pat. No. 5,040,198, I have disclosed a number of freestanding spot compression and magnification devices positionable on the imaging platform of conventional mammographic units to obtain high degrees of focal breast compression and high quality images of a mass. These devices have magnification platforms incorporating a spot compression pedestal which improves contrast and spatial resolution, and can disperse superimposed normal glandular tissue which at times interfere with evaluation of an abnormal area of the breast. Devices constructed in accordance with the invention include an open bottom base having an upper platform including an opening about which an upstanding pedestal is disposed, the pedestal being open at the bottom and having a flat top surface upon which the breast of a patient may be disposed and compressed by a conventional mammographic paddle. An air gap is provided between the upper surface of the pedestal and the imaging platform of the mammographic unit and provides improved radiographic contrast resolution and magnification to the image.

These devices as aforesaid were free standing, being positionable upon the imaging platform of conventional mammographic units without mechanical attachment thereto. Although such a free standing relationship is satisfactory for the low magnification devices, high magnification spot compression devices require the magnification platform to be attached to the imaging platform of the mammography unit, i.e., the normal breast supporting platform must first be disassembled by completely removing a cassette holder containing a moving grid called a "Bucky" tunnel device. The grid, as known in the art, acts similar to a filter and is required when nonmagnified imaging is performed. The magnifying platform is then attached directly to the imaging platform and the film or the cassette holder is inserted between the imaging platform and the magnifying platform. Thus, conversion from a nonmagnified or lower magnified platform to a high magnified platform is awkward and time consuming.

In order to overcome this problem, the aforesaid copending patent application proposed a base having adjustable clamping handles having a set of locking tabs which adjustably enter within the opening or tunnel of the cassette holder to engage and grasp the cover and secure the device in position. However, there are two known sizes of "Bucky" tunnel devices, i.e., 18×24 cm. and 24×30 cm. The locking tab construction of the adjustable clamping handles disclosed in the aforesaid copending patent application is adapted for use with one such device, i.e., the smaller one, and if the larger "Bucky" device is on the mammographic machine it must be removed and replaced by the smaller device before the spot compression and magnification platform may be mounted on the machine. The present invention is adopted to overcome this inconvenience.

SUMMARY OF THE INVENTION

Consequently, it is a primary object of the present invention to provide a spot compression and magnification device interposed between the breast of a female patient and the imaging platform of a mammographic unit, the device positionable on the cassette holder and an upstanding pedestal upon which the breast is positioned, the base of the device having adjustable means for permitting it to be connected to more than one of the standard breast supporting cassette covers or platforms of the mammographic unit so that it is not necessary to remove the known cassette holders containing the moving grid.

It is another object of the present invention to provide a spot compression and magnification device interposed between the breast of a female patient and the imaging platform of a mammographic unit, the device having a base positionable on the cover of the x-ray film cassette holder, which is the normal breast supporting platform, and an upstanding pedestal on which the breast is positioned, the base of the device having clamping handles including more than one set of locking tabs which adjustably engage into the opening or tunnel of more than one of the standard cassette holders to grasp the cover and secure the device in position.

Accordingly, the present invention provides a device as accessory for mammographic units for aiding in the spot compression of a female patient's breast to obtain a high degree of focal breast compression and magnification and thus to provide high quality x-ray images or views of a mass in the patient for greater diagnostic predictability. The device preferably is positionable directly upon more than one of the known cassette holders within which a moving grid is carried by means of adjustable clamping handles. The device includes a base having an open bottom and an upstanding pedestal opening into the base. The breast is positioned on the pedestal and is compressed between the device and a conventional mammographic paddle acting on the upper portion of the breast. The adjustable clamping handles are movable relative to the base so that the device may be attached to the cover of a multiplicity of mammographic cassette holders without requiring removal or replacement of the cassette holder.

In the preferred form of the invention the adjustable handles are connected to the base by biasing means which permit the handles to be pulled away from the sides of the base yet urge the handles toward the base, the handles having two sets of tabs or tongues which enter into the tunnel between at least two different size film cassette holder covers when the base is supported on the cover thereof. The tongues having respective ledges spaced beneath the base so as to abut the underside of the cassette holder covers when the base is disposed thereon.

BRIEF DESCRIPTION OF THE DRAWINGS

The particular features and advantages of the invention as well as other objects will become apparent from the following description taken in connection with the accompanying drawings in which.

DESCRIPTION OF THE PREFERRED EMBODIMENT

Figure 1:
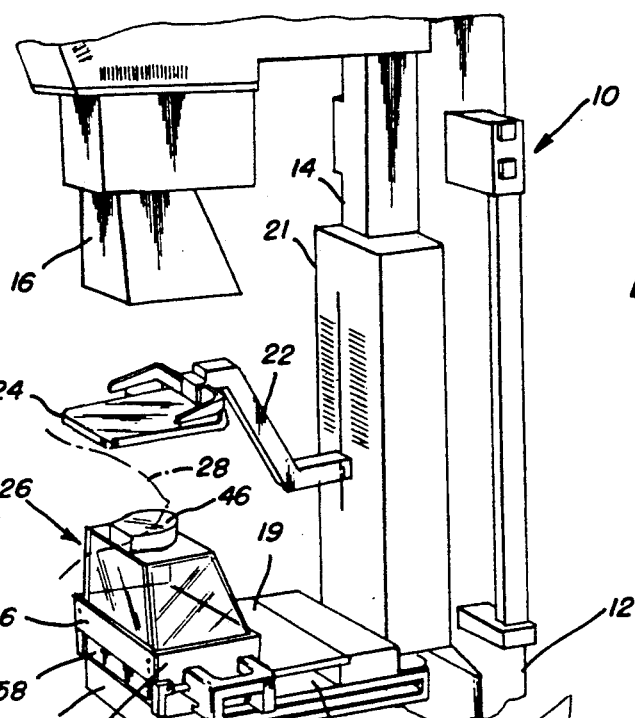
FIG. 1 is a fragmentary perspective view of a conventional mammographic unit with a spot compression and magnification device having adjustable clamping handles constructed in accordance with the principles of the present invention positioned on a cassette holder cover above the imaging platform thereof.

Referring now to the drawings, FIG. 1 illustrates a portion of a conventional relatively new type of mammographic unit 10, the unit comprising a frame 12 supporting a vertically adjustable column 14. The column 14 supports an overhanging head 16 which carries an x-ray source (not illustrated). Disposed below the head 16 is a vertically adjustable image platform 18, the platform generally having a cover member 19 disposed thereon and within which x-ray sensitive film is carried in, for example a film cassette (not illustrated), and a moving grid, the opening between the cover 19 and the surface of the image platform defining a "Bucky" tunnel 20, as is well known in the art. Conventionally, the breast of a patient is placed on the cover member which forms a breast support platform, overlaying the the film. Disposed about the column 14 is a housing 21 to which the arm 22 of a standard compression paddle 24 is attached. The arm may be vertically adjusted to lower the paddle 24 onto the upper portion of the breast to compress it against the cover member 19, the adjustment in at least some units being effected by pneumatic means. A small paddle with its own arm may be substituted for the standard paddle when conventional spot compression x-ray images or views are to be made of a suspicious area within the breast, the smaller paddle acting to concentrate or localize the compression force on a smaller area of the breast for a higher quality view as heretofore described. As aforesaid in many of the older mammographic units in current use spot compression paddles are not provided, nor are they readily available, and the units do not appear to have the capability of receiving such spot compression paddles. Accordingly, in these older units a spot compression view cannot be obtained and the results of the procedure may be equivocal.

A spot compression and magnification device 26 constructed as disclosed in the aforesaid copending patent application is disposed on the cover 19 of the platform 18 over the tunnel 20, and the compression paddle 24, either a standard or a spot compression paddle in those units having same, is lowered onto the breast 28 to compress the breast between the device 26 and the paddle 24 to obtain a high degree of focal breast compression. Thus, the spot compression and magnification device 26 may be utilized with either the newer or older mammographic units, and in the latter case may provide spot compression capabilities, and magnification, not currently available for such units. As aforesaid, spot compression views are particularly significant for many patients.

Figure 2:
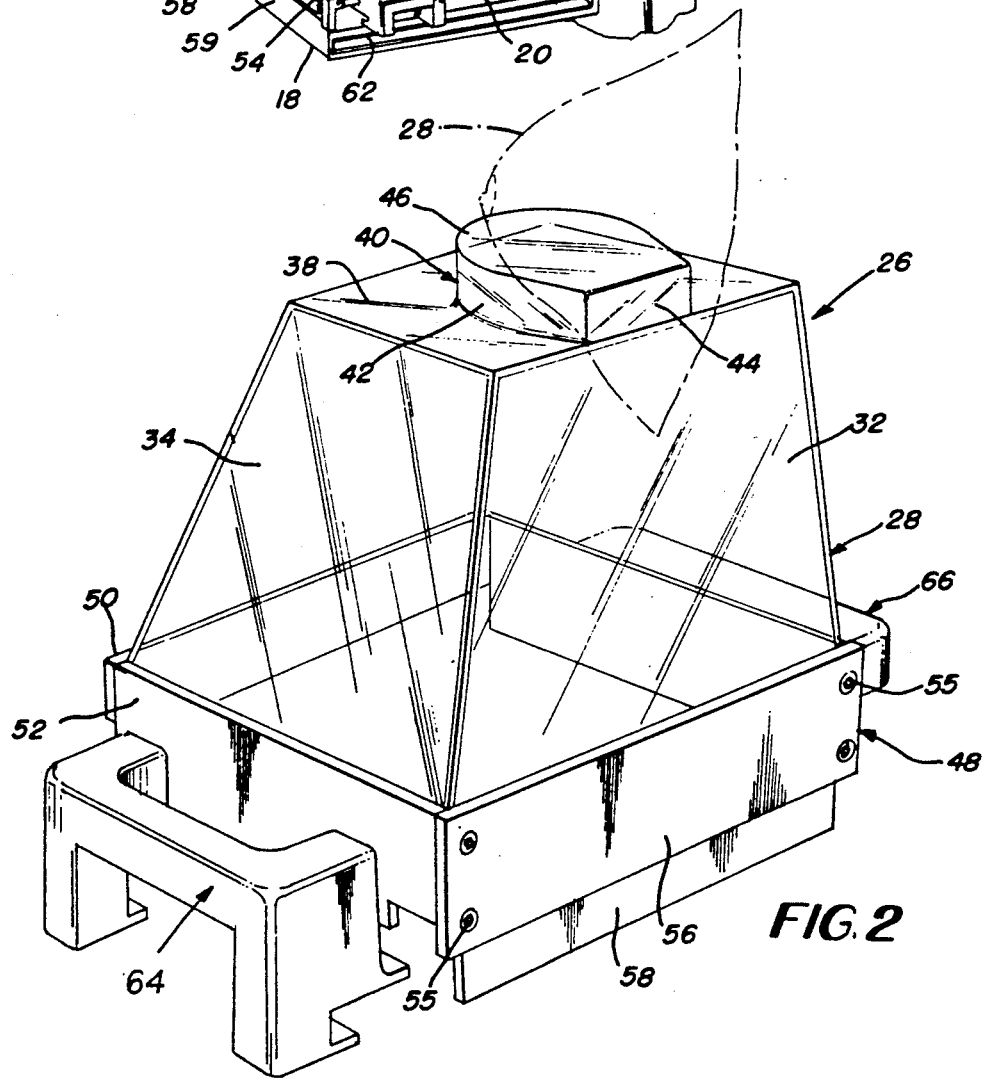
FIG. 2 is an enlarged perspective view illustrating the spot compression and magnification device illustrated in FIG. 1.
Figure 3:
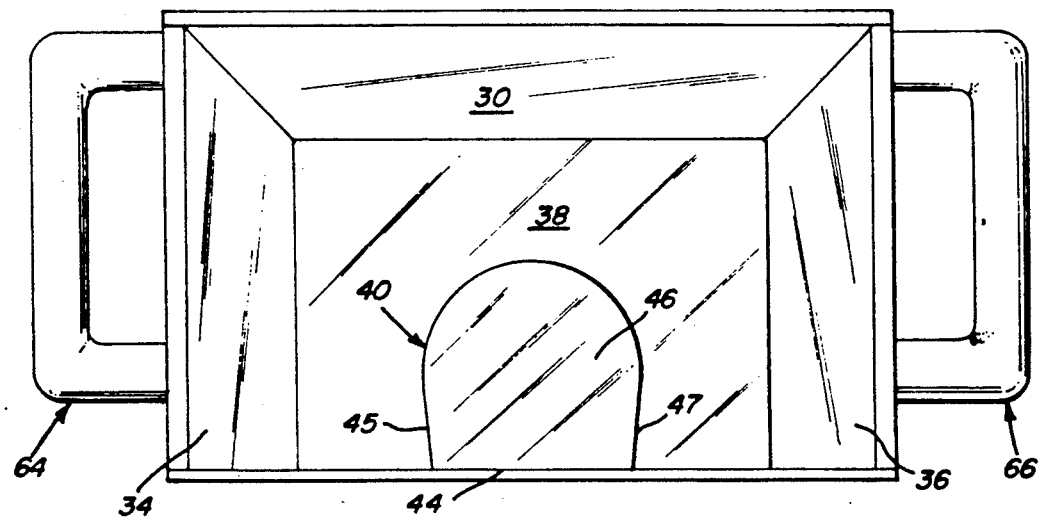
FIG. 3 is a top plan view of the spot compression and magnification device.

As illustrated in FIGS. 2 and 3, the device 26 comprises a base 28 having a substantially truncated pyramid configuration having a rectangular cross section including a front skirt 30 and a rear skirt 32 spaced apart by a pair of spaced apart end skirts 34, 36. The base, which is open at the bottom, includes an upper surface 38 having an aperture (not illustrated) formed therein, and a pedestal 40 is disposed on the upper surface overlying the aperture. The pedestal 40 is open at the bottom so as to open onto the interior of the base. Additionally, the pedestal 40 has a substantially truncated conical configuration with an upstanding peripheral wall 42. The peripheral wall 42 includes a flat rear portion 44 with the remaining portion being substantially circular, except adjacent to the rear portion 44 where there are a pair of flat surfaces 45, 47, a substantially flat upper surface 46 being disposed on the top of the wall 42 and conforming to the peripheral configuration thereof. The surfaces 45 and 47 could be circular, but for manufacturing ease they may be flat as illustrated. Thus, except for the flat rear portion 44, the pedestal is substantially conical.

The disposition of the pedestal is such that the bottom of the flat wall portion 44 may be very slightly offset from the rear skirt 32 of the base, or may be substantially aligned with the upper edge of the rear skirt 32, and although this disposition may vary slightly according to manufacturing methods and tolerances, it is important that the flat rear wall portion be disposed closely to the plane of the skirt 32 so as to abut the chest of a patient slightly beneath the breast while the skirt 32 abuts the chest and abdominal area. Moreover, the rear flat wall portion 44 of the pedestal may have a slight slope, in the order of approximately two degrees, flaring outwardly further at the bottom than at the upper surface 46. The remainder of the wall 44 may have a slight downward slope in the order of approximately two degrees so that the cross sectional configuration of the pedestal 40 is larger at the junction with the surface 38 of the base than at the upper surface 46 so as to provide a localized compression of the breast when the breast is compressed between the upper surface 46 and the paddle 24. The device as heretofore described may be disposed either on the cover 19 of the platform 18 or directly on the image platform 18 after removal of the cassette holder and moving grid. In either case the upper surface 46 of the pedestal 40 has a clear path to the cover member, thereby providing an air gap between the surface 46 and the cover member.

The spot compression and magnification device 26 preferably is formed from a synthetic plastic material, and it has been found that a transparent copolyester such as a polycarbonate such as that sold under the trademark LEXAN sold by General Electric Company may be used. Alternatively polyethylene Terephthalate Glycol-modified such as that sold under the trademark KODAR by Eastman Chemical Company of Kingsport, Tenn. may be used. These materials not only have a relatively high tensile strength, but have low x-ray radiation absorption characteristics.

A small spot compression and magnification device may have the lower edges of the base coated with a high friction material to preclude the device from moving over the imaging platform or the cover member, but for larger devices, i.e., those having greater magnifications, the device should be firmly attached to the imaging platform or cover. Thus, as illustrated for a large magnification device, the skirts of the base 28 for convenience may be attached to a sub-base 48. The sub-base preferably comprises a front rail 50 secured to a respective end rail 52, 54 by screws or the like 53, the end rails also being secured to a rear rail 56 by screws 55, the front and rear rails being longer than the front and rear skirts 30, 32 by an amount equal to the thickness of the end rails to form lap joints at the connecting interfaces for receiving the respective screws 53, 55 and the spacing between the interior of the end rails 52, 54 is slightly shorter than the length of the platform cover member 19. Additionally, screws or the like (not illustrated) are threaded from the interior of each of the skirts 30, 32, 34, 36 into the respective rail 50, 56, 52, 54 of the sub-base. The end rails 52, 54 and the rear rail 56 have a height which is longer than that of the front rail as best illustrated in FIG. 4 so that when the front rail is disposed on the upper surface of the cover 19, the other rails depend downwardly at the ends and the patient facing surface of the imaging platform cover 19.

Figure 4:
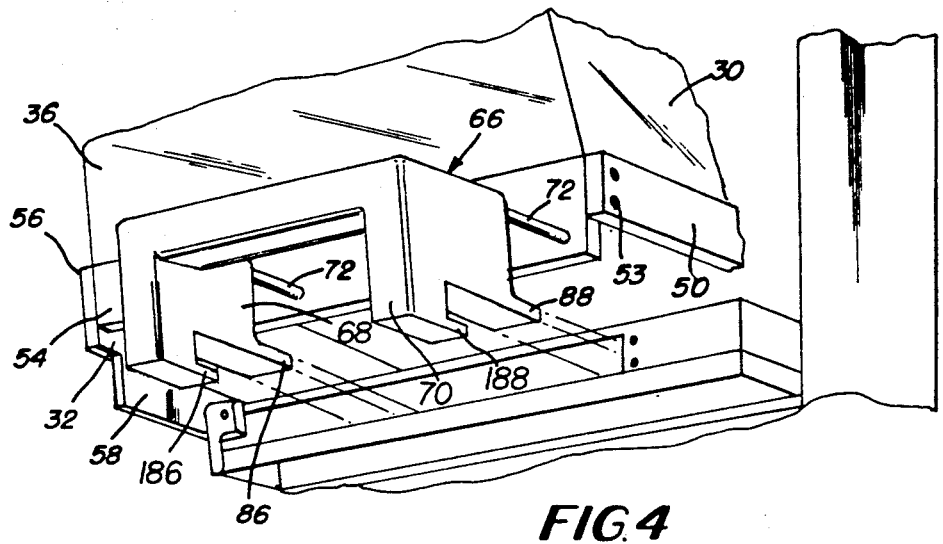
FIG. 4 is a fragmentary perspective view of the bottom portion of the device at one end thereof illustrating the manner of mounting the device on the mammographic unit.

Preferably, the bottom of the rear skirt 32 extends downwardly to the level of the lower edge of the rear rail 56, as illustrated in FIG. 4, and a downwardly depending lip member 58 is secured thereto, the lip member 58 extending to a level below the rear and end rails. Thus, the interior of the lip member 58, as illustrated in FIG. 1, may abut the upper portion of the corresponding patient facing surface 59 of the imaging platform cover 19 so as not to slide forwardly due to the action of the patient during the procedure. Moreover, the interior of each of the end rails 52, 54, as illustrated in FIGS. 5 and 6, preferably has an internally projecting ledge 60 spaced slightly above the bottom surface of these rails, the ledge being adapted to be received within grooves 62 in those instances where the device 26 is used directly on the imaging platform 18, i.e., where the cassette holder and the moving "Bucky" grid are removed from the mammographic unit 10.

As aforesaid, the device 26 has a substantially truncated pyramid configuration, the height of the base from the surface 38 being approximately 7 inches to the bottom edge of the front rail 50, and approximately 8½ inches to the bottom edges of the remaining rails, the bottom edge of the lip member 58 extending below the bottom edge of the rear rail 56 by approximately ⅜ inch. The wall thickness of the skirts 30, 32, 34, 36 and the surface 38 is approximately ⅛ inch. The opening at the bottom of the device defined between the interior of the rails is approximately 9½ inches by 6 inches while the surface 38 is approximately 6½ inches by 4¾ inches, the front to rear dimensions being smaller than that between the ends. The pedestal 40 preferably is glued or bonded to the surface 38 and has a height of approximately 1 inch, a diameter at the top surface 46 of approximately 3 inches excluding the flat wall surfaces 44, 45 and 47, the former being approximately 2 inches and the other two surfaces being approximately 1½ inches in length so that the front to rear distance across the top surface 46 is in the order of approximately 3 inches, the nominal wall thickness of the surface 46 and the wall 42 of the pedestal being approximately 1/32 of an inch or less. Thus, the total height of the device from the bottom edge of the front rail 50 to the top surface 46 of the pedestal 40 is approximately 8 inches which provides a magnification factor in the order of approximately 1.5. The precise height of the device will depend upon the distance between the x-ray source and the film, and this will vary with the different mammographic machines. Also the thin wall thickness of the pedestal and its mounting provides resiliency and permits sufficient depression of the back of the pedestal and compression of the posterior aspect of the breast.

In order to alleviate the need to disassemble the supporting platform, that is the removal of the cassette holder and the moving grid, so that the device 26 may be mounted on the top cover 19 of substantially all mammographic units, the present invention provides adjustable means for tightly clamping and grasping the ends and underside of the known "Bucky" tunnel covers 19 when the device is in place on the cover. To this end, clamping means in the form of an extendible handle 64, 66 having substantially U-shaped configurations in plan, is carried by the respective end rails 52, 54, the handles being molded from an appropriate synthetic plastic material. Each handle, as illustrated in FIGS. 4 through 6 with respect to the handle 66, has a pair of spaced apart legs 68, 70 which are connected to the respective end rail, e.g. rail 54, by means of a respective rod 72 (only one of which is illustrated). An enlarged head 74 on one end of the respective rod secures the rod to the rail at the interior thereof. The remainder of each rod 72 extends outwardly externally of the rail and is received through a bore 76 in the facing surface of the respective leg 68, 70, the bore 76 opening into a counterbore or hollow 78. Disposed about the rod within the hollow 78 is a coil spring 80 which compresses when the handle is pulled away from the device and thereby stores energy, the spring being constrained between the wall of the hollow 78 adjacent the bore 76 and the head of a screw 82 which is threaded into the adjacent end of the rod 72. A plug 84 closes the end of the hollow remote from the bore 76. Thus, when the handles 64, 66 are pulled away from the device and then released, the handles are urged by the springs into engagement with the respective end rail.

Figures 5, 6:
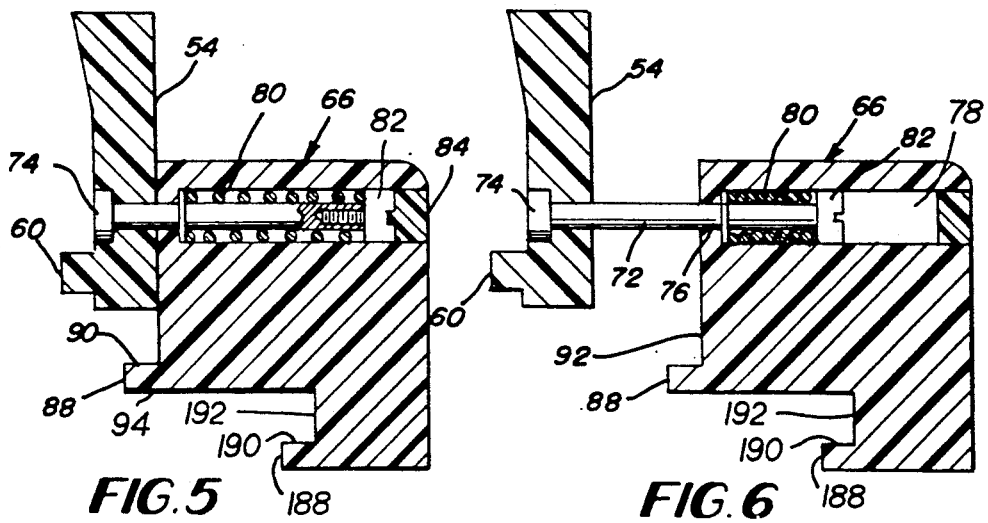
FIG. 5 is a cross sectional view through an adjustable clamping handle and a portion of the base of the device in the retracted or securing position.
FIG. 6 is a view similar to FIG. 5 but with the handle in the fully extended position permitting secure attachment of the base to a mammographic unit.

In accordance with the present invention each leg 68, 70 includes a pair of respective tongues 86, 88 and 186, 188 which project toward the interior of the device 26 and is spaced below the lower edge of the respective end rails 52, 54 as illustrated in FIGS. 5 and 6 with regard to the rail 54 and the tongue 88. The tongues 86 and 88 are effective when used with smaller of the two known "Bucky" devices, i.e., the 18×24 cm. size, while the tongues 186 and 188 are effective when used with the larger devices, i.e., the 24×30 cm. size. The tongues 86, 88 would be useful for cassette holders between these known sizes, while the tongues 186, 188 would be useful for cassette holders larger than these sizes. The spacing between the upper surface or ledge 90 of the tongue 88 and the bottom edge of the rail 54 when the handle abuts the rail is such as to grasp the smaller size cassette holder cover 19 therebetween while the interior facing surface 92 of each of the legs of the handles clamps against the respective end of the cover as the tongues 88 enter into the tunnel 20. On the other hand, the spacing between the upper surface or ledge 190 of the tongue 188 and the extended bottom surface 94 of the tongue 88 is such that when used with the larger "Bucky" device the interior facing surface 192 joining the surfaces 94 and 190 abuts the respective end of the cover and the surface 94 is disposed on the upper surface of the cover 19. Thus, the interior facing surface 92 abuts the smaller cover while the interior facing surface 192 abuts the larger cover. In the former case the tongues 88 enter into the tunnel 20 while in the latter case the lower and more externally disposed tongues 188 enter into the tunnel and the surface 94 of the handle rests on the top of the cover. Moreover, the handles 64, 66 not only act as clamps but also serve as carrying handles for manipulation of the device.

In use with the smaller of the known "Bucky" devices, the device 26 is placed on the cover 19 of the imaging platform 18, the bottom of the front rail resting on the cover and the interior of the rear rail 56 and the lip member 58 abutting and depending downwardly relative to the patient facing surface 59. The end rails are positioned at the edges of the cassette cover and the handles are pulled or extended away from the imaging platform so that the tongues 86, 88 and 186 and 188 are free of the opening 20. The handles are then released and retract due to the urging of the springs so that the tongues 86, 88 enter into the opening 20 and clamp the cover 19 between the surfaces of the ledges 90 and the bottom edges of the end rails while the surfaces 92 clamp against the respective ends of the cover. When used with the larger of the known "Bucky" devices, the device 26 is positioned on the cover in a similar manner but the end rails are disposed above the cover, and the handles are pulled to extend away from the imaging platform. When the handles are released and retract toward the cover, the tongues 186, 188 enter into the opening 20 and clamp the cover between the surfaces of the ledges 190 and the bottom surface 94 of the tongue 88 while the surfaces 192 clamp against the respective ends of the cover. In either case the center of the pedestal 40 is then disposed in superposed relationship over the x-ray film. The breast of a patient is then placed on the pedestal with the mass under consideration centered over the center of the pedestal. Pressure is then applied to the upper portion of the breast with the compression paddle 24 compressing the breast between the compression paddle and the device 26. The x-ray cassette is then inserted beneath the device through the space between the bottom edge of the front rail 50 and the cover 19 of the cassette holder.

Accordingly, the present invention provides a spot compression and magnification device which may be positioned readily on the top of the cover of the known film cassette holders over the imaging platform. The adjustable handles 64, 66 permit a rapid and simple attachment thereto without requiring removal of these cassette holders which contain the moving "Bucky" grid. By being interposed between the breast and the cassette holder devices constructed according to the present invention may be utilized with substantially all the known mammographic units.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A spot compression and magnification device positionable on the cover of at least two different size cassette holders selectively disposed on the breast supporting platform of mammographic apparatus for aiding in the spot compression of the breast of a female patient to provide x-ray images of localized portions of the breast, each of said covers being spaced above said platform and defining a tunnel therebetween, said device comprising a base having a polygonical cross section configuration including an upper platform and an open bottom defined between upstanding peripheral planar skirts, an aperture formed in said upper platform, an upstanding pedestal extending from said platform superposed about said aperture, said pedestal having an upstanding peripheral wall and a flat top surface adapted for receiving the lower portion of said breast, adjustable clamping means for adjustably attaching said device to the cover of either of said at least two cassette holders, means including biasing means for connecting said clamping means to said base and for permitting said clamping means to be extended manually from said base and resiliently urged toward said base, said clamping means including first and second sets of tongues disposed below the plane of said open bottom and projecting in a direction toward the interior of said base, each tongue of said sets of tongues having an upper surface and at least said first set of tongues having a lower surface spaced from the upper surface of a corresponding tongue of said second set, said first set of tongues being disposed closer to said base than said second set for entering into said tunnel and for engaging the upper surface of the respective tongue of said first set with a lower surface of the cover of a smaller of said holders when said base is positioned on the cover of said smaller holder, and said second set of tongues being disposed for entering into said tunnel and engaging the upper surface of the respective tongue of said second set with the lower surface of the cover of a larger of said holders when the lower surface of said first tongues is disposed on the cover of said larger holder.

2. A spot compression and magnification device as recited in claim 1, where in said clamping means comprises handles having a substantially U-shaped configuration in plan, said handles having legs depending downwardly therefrom, and said sets of tongues being disposed on and projecting from said legs.

3. A spot compression and magnification device as recited in claim 2, wherein said second tongues are disposed adjacent the bottom of said legs.

4. A spot compression and magnification device as recited in claim 2, wherein said legs include a first wall intersecting the upper surface of each tongue of said first set of tongues and a second wall extending from the lower surface of each tongue of the first set of tongues to the upper surface of each corresponding second tongue of the second set of tongues for engaging and clamping against ends of the covers of the larger and the smaller holders respectively when the respective tongues are within said tunnel.

5. A spot compression and magnification device as recited in claim 4, wherein each of said legs includes a hollow bore, said means for connecting said clamping means to said base comprising a rod having one end fastened to said base and extending into said bore, coil spring means disposed in said bore about said rod, means connected to another end of said rod for trapping said spring about said rod, said spring being compressed when said handles are pulled away from said base guided by said rods.

* * * * *